US00RE38423E

(19) United States
(12) Reissued Patent
Andersson

(10) Patent Number: US RE38,423 E
(45) Date of Reissued Patent: Feb. 10, 2004

(54) PROCESS FOR IN VITRO ANALYSIS OF TOXIC AND ALLERGENIC SUBSTANCES

(75) Inventor: Birger Andersson, Stockholm (SE)

(73) Assignee: Biovator Technologies AB, Kallered (SE)

(21) Appl. No.: 10/115,066

(22) PCT Filed: Jul. 3, 1996

(86) PCT No.: PCT/SE96/00902

§ 371 (c)(1),
(2), (4) Date: Dec. 9, 1998

(87) PCT Pub. No.: WO97/16732

PCT Pub. Date: May 9, 1997

Related U.S. Patent Documents

Reissue of:
(64) Patent No.: 6,046,010
Issued: Apr. 4, 2000
Appl. No.: 09/066,292
Filed: Dec. 9, 1998

(30) Foreign Application Priority Data

Nov. 1, 1995 (SE) ..... 9502409

(51) Int. Cl.[7] ..... G01N 33/53; G01N 33/567

(52) U.S. Cl. ..... 435/7.1; 435/7.2; 435/7.21; 435/325; 435/326; 435/372; 435/372.3; 435/373; 435/375; 530/351

(58) Field of Search ..... 435/7.1, 7.2, 7.21, 435/325, 326, 372, 372.3, 373, 375; 530/351

(56) References Cited

U.S. PATENT DOCUMENTS 5,439,799 A 8/1995 Rautenberg et al. ..... 435/793

OTHER PUBLICATIONS

McHugh et al., Allergy, V. 49, 1994, pp. 751–759.

C.G. Larsen et al., "The Delayed–Type Hypersensitivity Reaction is Dependent on IL–8. Inhibition of a Tuberculin Skin Reaction by an Anti–IL–8 Monoclonal Antibody," Journal of Immunology, V. 155, 1995, pp. 2151–2157.

M. Imada et al., "Allergen–Stimulated Interleukin–4 and Interferongamma Production in Primary Culture: Responses of Subjects with Allergic Rhinitis and Normal Controls," *Dialog Information Services,* File 155, Medline Dialog accession No. 09484227. Immunology, England, Jul. 1995, pp. 373–380.

K. Mueller–Decker et al., "Development of an In–Vitro Alternative Assay to the Draize Skin Irritancy Test Using Human Keratinocyte–Derived Proinflammatory Key Mediators and Cell Viability as Test Parameters," In Vitro Toxicol 5 (4) , *Dialog Information Services,* file 5, Biosis Dialog accession No. 10103327, Biosis accession No. 95103327, 1992, pp. 191–209.

R.V. House e tal., "In Vitro Evaluation Fentanyl and Meperidine for Immunomodulatory Activity," *Dialog Information Serices,* file 155, Medline accession No. 09556564, Immunol Letters, The Netherlands, May 1995, pp. 117–124.

J.D. Dewitte et al., "Improved HPLC Determination of Urinary Neopterin," *Dialog Information Serivces,* Biomed Chromatogr, England, 1987, pp. 183–188.

J.D. DeWitte et al., "Assay of Urinary Neopterin in Hypersensitivity Pneumopathies," Presse Med, France, 1986, p. 1932.

*Primary Examiner*—Prema Mertz
*Assistant Examiner*—Fozia Hamud
(74) *Attorney, Agent, or Firm*—Young & Thompson

(57) ABSTRACT

The invention concerns a process for in vitro evaluation of a potentially allergenic or tissue irritating substances, characterized in that blood cells are cultivated in the presence of serial dilutions of the substance whereby the highest concentration of the substance being non toxic to the cells is serial diluted, cell proliferation is measured and the presence of cytokines is measured whereby: the presence of one or more of the alarm cytokines of class 0 only is an indication of tissue damage and chemical toxic effects; the presence of one or more alarm cytokines of class 0 and possibly one or more cytokines of class IV type but not neopterin is an indication of delayed type hypersensitivity such as cellular immunity, delayed allergy and contact eczema; and the presence of one or more alarm cytokines of class 0 and at least neopterin and possibly one or more cytokines of class I is an indication of immediate type hypersensitivity such as asthma, hay fever, urticaria and rhinitis. The invention also concerns use of neopterin and IL-8 as analytic substances for distinguishing between the immune reactions type I and IV and a kit for analysis.

8 Claims, No Drawings

PROCESS FOR IN VITRO ANALYSIS OF TOXIC AND ALLERGENIC SUBSTANCES

Matter enclosed in heavy brackets [ ] appears in the original patent but forms no part of this reissue specification; matter printed in italics indicates the additions made by reissue.

CROSS-REFERENCE TO RELATED APPLICATIONS

This application is a 371 of WO97/16732.

The present invention concerns a process for in vitro analysis of toxic and allergenic substances. Substances intended for use as pharmaceuticals, food additives, cosmetic or hygienic products, industrial chemicals and other sub-stances are analysed for adverse reactions. Such reactions may be allergic reactions, skin irritating effects and toxic effects.

Today such tests are performed in vivo on animals. Animals are expensive to raise and keep. Further, some tests may involve suffering of the animals.

The present invention provides a process for in vitro analysis of the adverse effects of substances. The analysis of the substances is performed on blood cells from warm blooded animals. No animals are involved since the substances are tested on human cells i.e. cells from the same species as they are intended for. Some substances may not have the same effect on different species, and tests performed on animals may give false results. Therefore the test is preferably performed with human blood.

Thus, the method will be offered as an alternative to animal tests for food additives, cosmetic or hygienic products, industrial chemical, drugs and other substances where adverse reactions are to be avoided.

In vitro evaluation of toxic effects on the immune system has been tested on splenocytes from mice ("In vitro evaluation of drug-induced toxic effects on the immune system as assessed by proliferative assays and cytokine production", M. Pallardy et al. Eur. Cytokine Net., Vol. 2 No. 3, May–June 1991, pp. 201–206). The method was poorly effective detecting molecules inducing autoimmunity and hypersensitivity.

It has now turned out that according to the present invention it is possible to analyse adverse tissue reactions to foreign substances in vitro by cultivating them with human whole blood, prevented from coagulating and analysing the cytokine produced by the human cells.

Before a substance has been in use and before the target group has been exposed the present method offers the possibility to predict whether a risk for adverse reactions of inflammatory or allergic type will occur.

The invention provides an interpretation key for evaluating the adverse tissue reactions to foreign substances.

SUMMARY OF THE INVENTION

The method is defined in claim 1 and is based on cultivation of blood cells in vitro. The substance to be evaluated is added to the blood culture. If the reactive cells of the blood recognises the test material as foreign or damaging a production of inflammatory signal substances, cytokines occurs. The blood contains different white blood cells with different functions in the response to foreign substances. The different types of inflammatory cells secrete different repertoirs of cytokines. The patterns, (profiles) of the secreted cytokines indicate what compartment of the immune system that has been activated. Thereby is it also possible to predict what kind of adverse reaction to the expected from a substance if administered to humans or experimental animals. Some substances will induce a typical cytokine profile driving the immune system towards IgE mediated allergy, this indicating a potential of those substances to evoke asthma, hay fever and urticaria. Other substances will induce a cytokine pattern driving the immune system to cellular immunity thus having the potential to result in contact excema as an adverse reaction. Finally, a chemical or toxic effect will result in a cytokine pattern typical of alarm reactions seen in tissue damage and operations. Thus, the concept that the present method is based on is to use an interpretation of the cytokine pattern that a substance can induce in blood in vitro cells to predict whether the substance has the potential to cause allergy of different types or is generally hazardous to induce tissue damaging or toxic effects.

We classify adverse tissue reactions to foreign substances as follows.

Class 0: Tissue damage. Unspecific chemical, mechanical or physical damage.

Class I: Allergic immune reaction type I. This is also named immediate type hypersensitivity and is mediated by IgE antibodies produced specifically to the foreign substance. An acute inflammatory reaction is produced, histamine is often produced and examples of symptoms are asthma hay fever, urticaria and rhinitis. This type requires that the substance can induce a fully mature immune response where all components of the immune system participates. This is also considered as a final step immune reaction.

Class IV: Inflammatory immune reaction type IV. This is also named delayed type hypersensitivity and is mediated by sensitised T lymphoccytes type TH-I, considered as a first step type immune reaction. Allergic contact dermatitis is an example of this type of reaction.

Class 0 is our own classification of unspecific damage to the immune system. For Class I and Class IV see "Immunology" by Ivan Roitt, Jonathan Brostoff and David Male, Gower Medical Publishing London—New York, 1989, page 1.9–19.20 and 22.1–22.10, which is incorporated as a reference.

Three main types of cytokine profiles have been identified in the present work.

Class 0 type: Secretion of alarm cytokines indicating damage to connective tissue, fibroblasts, endothelial cells, epithelial cells and unspecific inflammatory white blood cells. Members of this group are IL-1, IL-6, IL-12 and TNF.

Class I type: Secretion of cytokines of an immune response type from lymphocytes and inflammatory cells. These includes cytokines from Class 0 and in addition IFN-gamma, Neopterin, IL-2 and IL-10. Theoretically as known from animal in vivo studies also IL-4 and IL-5 should be produced here, but these substances are notoriously difficult to determine and are therefore not routinely included in our test protocols.

Class IV type: Secretion of the cytokines of Class 0 unspecific type and in addition IL-2, IL-10 and IFN-gamma.

A finding that could not predicted was that the complete final type immune response Class I drives to Neopterin production whereas the Class IV primary type immune response does not stimulate the immune system as long as to Neopterin production.

In the three groups of cytokines listed above only preferably selected representative members are listed. The groups may contain other cytokines to be used and the patent is claimed for the use of analysis of all substances listed in The Cytokine Facts Book, Eds Callard R. E. and Gearing, A. J. H., Academic Press 1994 hereby incorporated as a reference and future updated issues to predict the grade of maturity of the response that a substance has the potential to evoke. At present 50 substances.

Interleukins

IL-1, IL-2, IL-3, IL-4, IL-5, IL-6, IL-7, IL-8, IL-9, IL-10, IL-11, IL-12, IL-13, IL-14, IL-15

Other Cytokines (in alphabetical order)

BDNF, CNTF, EGF, Epo, FGF, G-CSF, GM-CSF, I-309/TCA-3, γIP-10, INFα, IFNβ, IFNγ, LIF, LT(TNFβ), MCP-1,2 and 3, M-CSF, MIF, MIP-1α, MIP-I1β, MIP-2, NGF, NT-3, NT-4, OSM, PBP, PBSF, PDGF, PG-4, RANTES, SCF, TGFα, TGFβ, TNFα, Tpo, VEGF According to the invention the presence of inflammatory immune reaction type IV is preferably analyses by using IL-8. It has turned out that IL-8 is developed and is present in raised levels during type IV reactions.

Neopterin being present in higher amounts when type I reaction is at hand, IL-8 and/or neopterin can especially be used to distinguish between the inflammatory immune reaction type IV and the allergic immune reaction type I.

Based on the outcome of the in vitro test, the cytokine pattern induced by a the substance under investigation, a prediction will be made regarding the potential of the substance to cause adverse reaction if humans or animals are exposed to it. Whole blood, preferably venous blood is used. The blood is prevented from coagulating. This can be done by the use of endotoxin free heparin tubes. Other methods may also be used such as addition of EDTA or citrate. Alternatively the blood can be shaken with glass beads. The leukocyte counts in undiluted blood ranges between $3\times10^9$ and $7\times10^9$ per litre. Around 30% of these are lymphocytes and 5–10% are monocytes the rest being polymorfonuclear cells. Total leukocyte numbers and differential count is determined in a Coutler STKS cell haematology analyser before further procedure.

Whole blood is diluted serially from 1:1–1:1000, preferably 1:2–1:100 in a culture medium, preferably a tissue culture medium such as RPMI 1640 supplemented with glutamine. Normally, 1,5–5 mM, preferably 2 mM is used. The blood is most often diluted 1:5, 1:10 1:20 or continued to 1:40, 1:80, 1:100.

Antibiotics are preferably added to prevent the growing of unwanted microorganisms. Penicillin and streptomycin may be added in concentrations of 25–100 U/ml, preferably 50 U/ml.

Mitogens or substances with known effects on the immune system can be used as positive controls to give better results. Any mitogen as mentioned in Daniel P. Sites: Clinical Laboratory Methods for Detection of Antigens & Antibodies in.Basic and Clinical Immunology, Lange Medical Publications, Los Altos, Calif., 1984 may be used. This reference is incorporated in this description by reference. Phytohemagglutinin (PHA-L) is preferably used and dissolved in the medium to a final concentration of in the wells of 250 μg per ml.

The test can be performed in any suitable vessel e.g. in tubes or preferably in the wells of microtiter plates.

For triggering cytokine production in vitro the cell concentration is of critical importance. If the test is performed only at one cell concentration, then only some of the cytokines of interest will be optimally detected. If a series of cell concentration is used the complete picture of the cytokine pattern predicted above in "Summary of the invention" is revealed.

For substances to be tested for effects in the system different concentrations are added to the blood. The highest concentration of the substance being non toxic to the cells indicated by inspection in microscope in presence of vital stain e.g. trypan blue is used as start concentration. Serial dilution of the substance is then performed down to a dilution of at least 1:1 000 and preferably down to 1:10 000, 1:1000 0000 or 1:1 000 000.

In cases where the substance is diluted in RPMI 1640 the appropriate control is medium only. When other diluents are used, controls of the appropriate diluent at corresponding concentrations are used.

The vessels are incubated at 25–40° C., preferably at 37° C. at 50–95%, preferably 90% humidity and preferably in the presence of with 2–15% $CO_2$, preferably 5%. An appropriate number of tubes or microtiter plates are prepared and are taken out of the incubator for testing at the intervals. Standard time intervals are 1 hour, up to 10 days; preferably 1 hour 1 day, 2 days and 4–6 days.

Proliferation assay can be made as follows. One set of plates is used to estimate the proliferative activity of the donor cells spontaneously (=medium) or substance dissolvent controls), in response to mitogens and in response to samples of test substances at various concentrations This can be done as follows or by any other suitable method. At time intervals plates are tested, and to each well in the plate is added labeled nucleic acid precursor such as $^3$H-thymidine dissolved in the medium. The plates are incubated for additional 4 hours 37° C. for incorporation of labeled nucleic acid precursor. The cells are then collected using a Skatron cell harvester (Skatron, Lier, Norway) and Titertek paper filters or any other suitable method. The result of this procedure is that the DNA of the cells is captured in the filter paper, whereas the $^3$H-thymidin not incorporated in the DNA passes through the filter and goes with the waste washing water. The radio-activity in the filter papers is thus proportional to the DNA synthesis that occured during the 4 hours preceding the harvesting procedure. The radioactivity of the filter papers is determined in a Packard liquid scintillation counter, and thymidine incorporation is expressed as counts per minute (cpm) The radioactivity or any other label of the precursor can be measured in DNA harvested by any other mechanical or chemical way and measured by any suitable isotropic or chemical instrument.

Cytokine Assays:

Another set of plates is prepared with the same design as in "Culture protocoll" above. Also here, plates are removed from the incubator at various time intervals, and cytokines released from the cultured cells are measured in the supernatants obtained after centrifugation of the plates at 650 g for 10 minutes. The supernatants can either be tested immediately or stored at −20° C. until tested. For cytokine determinations diagnostic kits of various origins are used. The present procedure may use any available or newly constructed test using cytokine quantitation including bioassays, immunoassays or chemical assays or other.

The instructions of the manufacturers are followed. All these tests are enzyme immunoassays (EIA:s). The principle is that microtiter plate wells are labeled with a cytokine specific capture antibody. If cytokine is present in the samples added to the wells it will be captured to the bottom of the well. To quantitate how much cytokine that has been captured a second antibody, labeled with an enzyme is added to the wells. The reaction is thereafter measured as colour developed after addition of a substrate for the enzyme. The values for the test wells is compared with a standard curves obtained from a series of known amounts of cytokine. The values for control wells with no substance added to the cells are used as background levels for the tests. Positive indications are recorded when values above 2 SD of the variation are obtained.

The invention also concerns a kit comprising one or more reagents recognizing the alarm cytokines of class zero, and/or the cytokines of class I type, and/or the cytokines of class IV. Examples of such cytokines are mentioned above. Reagents reacting for the presence of neopterin and IL-8 are preferred.

These reagents may be antibodies or any other reagents that are sensitive for these substances. The reagents may be supported by a carrier such as a strip, titer plates, micro-titer plates, Eliza plates, test tubes etc. The carriers may be of different sizes. The carrier material may be any solid or semi-solid material that does not interfere with the reaction between the reagent and the cytokine. The carrier can take on a variety of shapes and compositions, including microparticles, beads, porous and impermeable strips and membranes, the interior surface of reaction vessels such as test tubes and microtiter plates, and the like. Microtiter plates and beads may be of plastic, such as styrene or acryl-polymers or glass. Nitrocellulose can be used, preferably in the form of filters, strips or discs. Means for attaching a desired reaction partner to a selected solid support will be a matter of routine skill to the worker in the field. It is also possible to use flow cytometer.

The invention will now be better described with the following non limiting examples.

EXAMPLE

Blood Donors and Blood Collection:

Five healthy blood donors from both sexes ranging in age between 25 and 55 years are used. Blood is collected by venous puncture into endotoxin free heparin tubes (Coatech, Ljungby, Sweden) that contains 120 IU heparin and are filled with 4 ml of blood. None of the blood donors are allowed to have a history of allergy or atopic excema or any indication of ongoing disease of any kind.

Cell Analysis:

Total and differential white blood cell counts are measured with Coulter STKS equipment. The five donors had total white blood cell counts of 9,8; 7,1; 9,8; 6,9; 5,8; $10^9/1$.

Culture Protocol:

The whole blood is diluted serially 1:2, 1:3, 1:20, 1:4, and 1:10 in tissue culture medium, RPMI 1640 supplemented with 2 mM glutamine, 50 U/ml of penicillin and 50 Ug/ml of streptomycin. 100 ul of blood is added to the wells of Nunclon microtiter plates. The mitogen phytohemagglutinin (PHA-L)(L-4144, Sigma St Louis USA)is dissolved in RPMI 1640 and 50 ul of the solution is added to the wells so that a final amount of 25 $\mu$g per well is achieved.

For substances to be tested for effects in the system different concentration are added to the blood. The highest concentration of the substance being non toxic to the cells indicated by inspection in microscopic in presence of vital stain e.g. trypan blue is used as start concentration. The following substances and concentrations were used: 0=Triton×100 in concentrations 1:2000, 1:4000, 1:8000, 1:160000, 1:32000, 1:64000, 1:128000 IV=$NiCl_2$ 100 $\mu$g, 10 $\mu$g, 1 $\mu$g, 0,1 $\mu$g, 0,01 and 0,001 $\mu$g per ml I=mite extract (1:10, 1:20, 1:40, 1:80 Pos=PHA 25 $\mu$g per well (200 $\mu$l)

In cases where the substance is diluted in RPMI 1640 the appropriate control is medium only. When other diluents are used, controls of the appropriate diluent at corresponding concentrations are used.

Incubation:

The microtiter plates are incubated at 37° C. at 90% humidity and with 5% $CO_2$. An appropriate number of of identical plates are prepared and are taken out of the incubator for testing at intervals of, 1 day, 2 days and 6 days.

Proliferation assay:

One set of plates is used to estimate the proliferative activity of the donor cells spontaneously (=medium or substance dissolved controls); in response to PHA, and in response to samples of test substances at various concentrations. The highest concentration of sub-stance non toxic to the cells indicated by inspection in microscope in presence of vital stain (e.g. trypan blue) is used as start concentration. Ser. dilutions of the sub-stance is then performed as stated above.

To each well in the plate was added 1 uCi of $^3$H-thymidine (Amersham International, Amersham UK; 50 Ci/mM) in 50 ul of RPMI 1640. The plates were incubated for additional 4 hours at 37° C. The cells were then collected using a Skatron cell harvester (Skatron, Lier, Norway) and Titertek paper filters. The result of his procedure is that the DNA of the cells is stuck in the filter paper, whereas the $^3$H-thymidin not incorporated in the DNA passes through the filter and goes with the waste washing water. The radioactivity in the filter papers is thus proportional to the DNA synthesis that occured during the 4 hours preceding the harvesting procedure. The radiactivity of the filter papers is determined in a Packard liquid scintillation counter, and thymidine incorporation was expressed as counts per minute (cpm).

Cytokine Assays:

Another set of plates is prepared with the same design as in "Culture protocol" above. Cytokines released from the cultured cells are measured in the supernatants obtained after centrifugation of the plates at 650 g for 10 minutes. The supernatants were either tested immediately or stored at −20° C. until tested.

For information only is here mentioned that in the tests performed the following commercial kits and manufacturers were used.

IL-beta: Immunotech, Chromgenix
IL-2:Immunotech, Chromgenix
IL-4:R&D Systems
Neopterin: Henning Berlin
IL-6:Immunotech, Chromgenix
IL-8:Assay Res. Inc
Interferon-gamma: Genzyme
sCD8:T Cell Diagnostics
sIL-2R Immunotech
TNF: Medgenix
IL-10:Medgenix The instructions of the manufacturers were followed. All these tests are enzyme immunoassays (EIA:s). The principle is that microtiter plate wells are labeled with a cytokine specific capture antibody. If cytokine is present in the samples added to the wells it will be captured to the bottom of the well. To quantitate how much cytokine that has been captured a second antibody, labeled with an enzyme is added to the wells. The reaction is thereafter measured as colour developed after addition of a substrate for the enzyme. The values for the test wells is compared with a standard curve obtained by adding a series of known amounts of cytokine. The values obtained for control wells with no substance added are used as background values for cytokine levels and proliferation as measured by $^3$H-thymidin incorporation. Positive indications are recorded when values above 2 SD of the variation of the controls are obtained.

The results from testing three substances with previously from clinical experience known properties, but not previously tested with the method are shown:

0. Triton X-100 This is a detergent with tissue damaging effects. Dissolves cell membranes.
I. Dust mite antigen (Soluprick, ALK Sverige AB). This preparation is made from an extract of dust mites and is used clinically to test for immediate type allergy by intracutaneous injection.
IV. Nickel chloride (Sigma St Louis, USA). This metal is wellknown as a cause of delayed type allergy (contact excema) in humans and experimental animals.
Plus. The positive indicator of responsiveness of the system the calibrator was the mitogen PHA (Sigma, St louis, USA).

TABLE I

In vito performance test
Values for 11 cytokines and $^3$H-Thymidine Proliferation. Obtained after stimulation of blood from 5 normal humans. All values are related to medium control given the value 100.

| | IL-1 | TNF | IL-6 | IL-8 | IL-2 | STL-2R | SCD8 | IL-10 | IL-4 | $IFN_\gamma$ | Neopterin | Prolif. Index |
|---|---|---|---|---|---|---|---|---|---|---|---|---|
| O | 630 | 400 | 460 | 200 | 85 | 115 | 95 | 95 | 85 | 120 | 110 | 200 |
| IV | 1165 | 225 | 660 | 380 | 445 | 130 | 110 | 800 | 80 | 1220 | 90 | 1340 |
| I | 320 | 240 | 250 | 100 | 900 | 120 | 85 | 640 | 900 | 800 | 560 | 120 |
| Plus | 690 | 420 | 1620 | 780 | 750 | 1820 | 940 | 1250 | 820 | 800 | 440 | 2600 |

The highest value as compared to medium control obtained at any time or concentration for each substance is used as indicator value in the table and related to medium control put to value 100 index.

Results:

In summary the results of a performance example are presented below and the stimulatory effects were quite different for the different compounds.

0. Triton X-100 induced proliferation. Cytokines of the unspecific tissue toxic group were induced i.e. IL-1, IL-6 and TNF. This is a positive tissue irritant.

I. Dust Mite:

Induced no proliferative response. Substances secreted into supernatants were the unspecific inflammatory IL-1, TNF and IL-6 and of immune lymphocyte class the IL-2, IL-4, IL-10 and IFN-gamma. Furthermore the Neopterin typical for induction of specific immune responses of a late mature stage. There is a potential for antibody and IgE production.

IV. Nickel chloride: Induced a low proliferative response. The cytokines induced were the unspecific inflammatory mediator IL-1, IL-6, TNF and IL-8. Of the immune lymphocyte class IFN-gamma, IL-2 and IL-10 were induced, but notably no Neopterin.

Plus. PHA:

Induced a strong proliferative response indicated by $^3$H-thymidine incorporation and also cell types of cytokines were induced. The substances secreted in the supernatants included: Cytokines of primary inflammatory type as IL-1, IL-6, TNF and IL-8. Cytokines of the types typical for specific immune responses both early and late as neopterin, IFN-gamma IL-2 and IL-4 and IL-10 typical of both early and late responses were induced.

What is claimed is:

1. A process for in vitro evaluation of a potentially allergenic or tissue irritating substance, comprising: cultivating blood cells in the presence of the substance, [and serially diluting said substance to obtain the highest concentration of the substance that is non-toxic to the cells; i) measuring cell proliferation; ii) assaying for secreted Il-8 and neopterin and iii)] *assaying for secreted IL-8 and neopterin, and* comparing relative amounts of secreted IL-8 and neopterin to distinguish between class I and class IV cytokine profiles for the substance, wherein higher IL-8 levels is an indication of class IV cytokine profile and pro-inflammatory immune reaction and higher neopterin levels is an indication of class I cytokine profile and pro-allergenic immune reaction.

2. The process according to claim 1, further comprising measuring class 0 cytokines selected from the group consisting of IL 1, IL-12, IL-6, and TNF.

3. The process according to claim 1, *further comprising serially diluting said substance to obtain a highest concentration of said substance that is non-toxic to the cells,* wherein the substance to be tested is presented in the highest concentration being non toxic and in a serial dilution thereof at least 1:1000.

4. The process according to claim 3, wherein [the] *a* serial dilution is performed down to a dilution of at least 1:10 000 to 1:1 000 000.

5. The process according to claim 1, wherein the blood is diluted serially from 1:1 to 1:1000.

6. The process according to claim 1, wherein whole blood is treated to not coagulate, diluted 1:2–1:100 in tissue culture medium preferably supplemented with glutamine and/or an antibioticum, a marked nucleic acid precursor is added, the substance to be tested is serially diluted down to a dilution of 1:1000 to 1:1 000 000 from the highest concentration of the substance being non toxic to the cells as indicated by inspection in microscope in presence of vital stain and added in different concentrations and incubated at 25C–40C, and tested at time intervals from 1 hour to 6 days by certifying that proliferation has taken place by collecting the cells on filter paper or harvesting nucleic acid by any other mechanical or chemical method and analyzing the labeled nucleic acid precursor.

7. A reagent kit for use in the process according to claim 1, comprising reagents specific to each of IL-8 and neopterin.

8. The process according to claim 1, wherein the blood is diluted serially from 1;2 to 1:100.

* * * * *